United States Patent [19]

Szebeni et al.

[11] 4,228,164
[45] Oct. 14, 1980

[54] CONDENSED PURINE DERIVATIVES USEFUL FOR IMPROVING PERIPHERAL CIRCULATION

[75] Inventors: Rudolf Szebeni; Dezső Korbonits; Kálmán Harsányi, all of Budapest; Molnár Leventéné, Szödliget; László Szekeres; Gyula Papp, both of Szeged; Gyula Sebestyén, Budapest, all of Hungary

[73] Assignee: Chinoin Gyogyszer es Vegyeszeti Termekek Gyara Rt., Budapest, Hungary

[21] Appl. No.: 958,526

[22] Filed: Nov. 7, 1978

[51] Int. Cl.² .............. A61K 31/54; A61K 31/52; C07D 473/08; C07D 513/14
[52] U.S. Cl. ............... 424/246; 424/253; 544/34; 544/251; 544/272
[58] Field of Search .......... 544/34, 251; 424/246, 424/253

[56] References Cited

U.S. PATENT DOCUMENTS 3,637,684  1/1972  Goldman .................. 544/251
4,073,908  2/1978  Quelet .................... 544/251

Primary Examiner—Paul M. Coughlan, Jr.
Attorney, Agent, or Firm—Karl F. Ross

[57] ABSTRACT

A compound of the formula

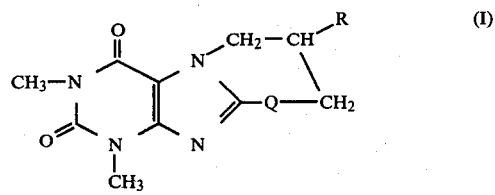

wherein
R is hydroxy, alkoxy or acyloxy
Q is sulfur or a $=N-R^1$ group, wherein $R^1$ is hydrogen, $C_{1-5}$ alkyl or aralkyl or $C_{2-4}$ acyl, or a pharmaceutically acceptable acid addition salt thereof.

10 Claims, No Drawings

CONDENSED PURINE DERIVATIVES USEFUL FOR IMPROVING PERIPHERAL CIRCULATION

The present invention relates to new condensed theophylline derivatives of the formula (XIX)

and acid addition salts thereof and a process for the preparation thereof.

In the formula I

R is hydroxy, $C_{1-4}$ alkoxy or acyloxy,

Q is sulfur or $=N-R^1$ wherein $R^1$ is hydrogen, $C_{1-5}$ alkyl or aralkyl or $C_{2-4}$ acyl.

Compounds of the formula I have therapeutic activity in heart therapy and in peripheral circulation without being toxic.

The compounds of the formula I may be prepared by (a) abstracting hydrohalogenic acid from compounds of the formula (XIIX)

wherein X is halogen—with or without isolating the optionally formed intermediate product of the formula (XIIIX)

or (b) abstracting hydrohalogenic acid from compounds of the formula (XIVX)

wherein Q, R, $R^1$ and X are as defined above—with or whithout isolating the optionally formed compounds of the formula (XVX)

or (c) reacting compounds of the formula (XVIX)

wherein Q is as given above—with compounds of the formula (XVIIX)

wherein X is halogen—in order to prepare compounds of the formula I wherein R is hydroxy, or (d) reacting compounds of the formula (XVIIIX)

wherein X is as defined above—with compounds of the formula $$H-Q-H \quad (XIXX)$$

wherein Q is $=N-R^1$ in order to prepare a compound of the formula I wherein R is hydroxy and Q is $=N-R^1$ or (e) reacting compounds of the formula (XXX)

with an alkylating and/or acylating agent in order to prepare compounds of the formula I—wherein R is acyloxy or alkoxy, Q is sulfur or $=N-R^1$, wherein $R^1$ is acyl or alkyl as given above—or (f) hydrogenolyzing and/or hydrolyzing compounds of the formula

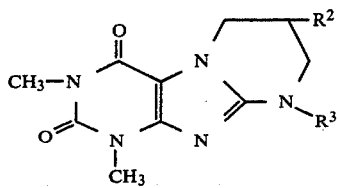

wherein R² is hydroxy or acyloxy, as given in the definition of R and R³ is hydrogen, benzyl or acyl as given in the definition of R¹, provided when R² is hydroxyl R³ cannot be hydrogen—in order to prepare a compound of the general formula X—wherein Q is =N—R¹, wherein R¹ is as defined above—falling under the scope of the scope of the compounds of the formula I, or (g) hydrolyzing a compound of the formula

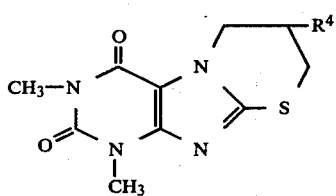

wherein R⁴ is acyloxy as given in the definition of R and, if desired, converting the obtained compounds to a salt by reacting it with an organic or inorganic acid and setting it free from the salt thereof—in order to prepare a compound of the formula

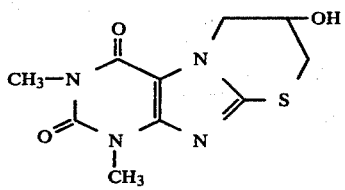

falling under the scope of the compounds of the formula I.

When abstracting hydrohalogenic acid in method steps (a) and (b) according to the invention, the reaction may be carried out in an organic solvent, such as an alcohol in the presenco fo the generally used inorganic bases, such as sodium hydroxide, potassium hydroxide, sodium carbonate or potassium carbonate, sodium hydrogen carbonate or potassium hydrogen carbonate by heating the mixture, preferably at the boiling point of the solvent. The hydrohalogenic acid may be abstracted from compounds of the formula VII as well—wherein X is as given above—using the compounds of the formula VII as a solvent.

When carrying out method step (c) according to the invention compounds of the formula VII may be used in excess (method c)1) or in an equimolar amount (method c)2). In the case of method c/1 no other solvent is used and the compounds of the formulae VI and VII are directly heated, preferably at the boiling point of the compounds of the formula VII. In the case of method c/2 the compounds of the formulae VI and VII are reacted in a solvent, such as ethyl, methyl, propyl, iso-propyl alcohol or benzene, toluene or some other organic solvent in the presence of a generally used base, such as sodium hydroxide, potassium hydroxide or an alkali metal carbonate by heating the mixture preferably at the boiling point of the solvent.

Method step (d) according to the invention is preferably carried out in an organic solvent, such as ethyl alcohol, benzene, toluene, by heating the mixture preferably at the boiling point of the solvent, in the presence of a generally used base, such as sodium or potassium hydroxide, ensuring the abstraction of the hydrogen-halogenic acid.

In method step (e) according to the present invention the acylation may be carried out according to known methods, preferably with acylating agents, such as acid anhydrides, acid halides, in the presence of an acid binding agent, such as tertiary amines. In the course of acylation inert solvents, such as benzene or acetone may be used, but the acylating agent itself e.g. acetic acid anhydride may serve as a solvent.

The alkylation may be carried out with a generally used alkylating agent, such as alkyl halides, alkyl sulfates, preferably in the presence of an organic solvent and an acid binding agent. As an acid binding agent alkali metal hydroxide, carbonate, hydrocarbonate, particularly potassium carbonate are preferred and as a solvent preferably alcohols, acetone or dimethylformamide may be used.

The desacylation according to method step (f) may be carried out by heating with an acid or by treatment with a base. As an acid hydrochloric acid is preferred.

The hydrogenolysis of the benzyl group may be performed by a conventional catalytic hydrogenation in an organic solvent, in the presence of a metal catalyst. A particularly preferred embodiment of the process is to carry out the hydrogenation in a 10:1 mixture of ethanol and concentrated hydrochloric acid in the presence of charcoal on a palladium catalyst.

The compounds of the general formula I according to the invention and non-toxic acid addition salts thereof may be used as active ingredients of pharmaceutical formulations containing also non-toxic inert pharmaceutical acceptable organic or inorganic carriers. The compositions may be finished in solid form, such as tablets, dragees, pills, etc., or in liquid form, such as suspensions, solutions or emulsions. Some examplex of the carriers which may be employed are talc, starch, gelatine, water, polyalkyleneglycols. The compositions may contain other excipients too, such as wetting agents, emulsifying, suspending agents, salts and buffers promoting the change of osmotic pressure, disintegrating agents and/or further therapeutically active ingredients.

The invention is further illustrated by the following non-limiting Examples:

EXAMPLE 1

19.90 g. (0.00526 mole) of 8-benzylamino-7-2-hydroxy-3-chloropropyl(-theophylline) and 236.0 g. of epichlorohydrine are heated for 10 hours whereafter the solution is evaporated. 1,3-Dimethyl-2,4-dioxo-7-hydroxy-9-benzyl-6,7,8,9-tetrahydro-pyrimido[2,1-f]purine melting at 225°–227° C. is obtained.

The pharmacological test results of the compound are favorable. No toxic effect was noticed, $LD_{50} > 3000$ mg./kg. in mice. The blood pressure is reduced at a dose of 0.5–2.0 mg./kg. The frequency of respiration is increased by 22% upon administration of a dosage of 1 mg/kg, by 41% on administering a dosage of 2 mg/kg, while the minute and arterial volume remains unchanged. The coronary perfusion is increased by 30% on administration a dosage of 0.5 mg/kg and by 60% upon an administration of a dosage of 2 mg/kg. The effect is similar (the same order of magnitude) to the effect of papaverine. The compound shows a particularly favorable activity on the femoralis artery region. The perfusion is enforced by 32% at a dose of 0.5 mg/kg.

EXAMPLE 2

0.77 g. (3.0 mmole) of 2,3-dioxo-1,3-diethyl-7-hydroxy-6,7,8,9-tetrahydro-pyrimido[2,1-f]purine, 0.39 g. (3.0 mmole) of benzyl chloride, 0.22 g. of anhydrous potassium carbonate and 22 ml. of anhydrous dimethylformamide are heated for 4 hours. The reaction mixture is worked up and thus 1,3-dimethyl-2,4-dioxo-7-hydroxy-9-benzyl-6,7,8,9-tetrahydro-pyrimido[2,1-f]purine is obtained. M.p.: 226°–228° C.

EXAMPLE 3

1.0 g. (3.5 mmole) of 8-benzylaminotheophylline and 10 ml. of epichlorohydrine (0.196 mole, 18.2 g.) are heated for 10 hours. By working up the mixture 1,3-dimethyl-2,4-dioxo-7-hydroxy-9-benzyl-6,7,8,9-tetrahydro-pyrimido[2,1-f]purine is obtained. M.p.: 226°–228° C.

EXAMPLE 4

2.7 g. (10 mmole) 2,4-dioxo-1,3-dimethyl-7-chloromethyl-1,2,3,4,6,7-hexahydro-oxazolo[2,3-f]purine, 1.07 g. (10 mmole) benzylamine and 50 ml. ethylalcohol are heated for 5 hours and 0.4 g. (10 mmole) of sodium hydroxide are added within 3 hours under further heating. After working up the reaction mixture 1,3-dimethyl-2,4-dioxo-7-hydroxy-9-benzyl-6,7,8,9-tetrahydro-pyrimido[2,1-f]purine of a melting point: 226°–228° C. is obtained.

EXAMPLE 5

(a) 5.0 g. (17.4 mmole) of 7-(2-hydroxy-3-chloropropyl)-8-aminotheophylline and 0.7 g. (17.4 mmole) of sodium hydroxide are heated for 3 hours in 600 ml. of ethyl alcohol.

The reaction mixture is worked up to give 1,3-dimethyl-2,4-dioxo-7-hydroxy-6,7,8,9-tetrahydro-pyrimido[2,1-f]purine. M.p.: 360° C.

(b) 1.9 g. (6.65 mmole) of 7-(2-hydroxy-3-chloropropyl)-8-aminotheophylline and 16 ml. of epychlorohydrin (22.47 g. 0.243 mole) are heated for 10 hours. Working up the reaction mixture a product identical with the product of 5a is obtained.

EXAMPLE 6

0.6 g. (1.45 mmole) of 1,3-dimethyl-2,4-dioxo-7-hydroxy-9-benzyl-6,7,8,9-tetrahydro-pyrimido[2,1-f]purine are dissolved in 90 ml. of 1:1 mixture of alcohol and hydrochloric acid and the mixture is hydrogenated at 1 atm at 25° C. using a Pd/C catalyst. The catalyst is removed, and the solvent is also removed, whereafter 1,3-dimethyl-2,4-dioxo-7-hydroxy-6,7,8,9-tetrahydro-pyrimido[2,1-f]purine is obtained. M.p.: 360° C.

EXAMPLE 7

1.1 g (5.2 mmole) of 8-mercapto-theophylline, 0.47 g. (5.0 mmole) of epichlorohydrine, 0.52 g. (5.2 mmole) of anhydrous triethylamine and 5 ml of n-propyl-alcohol are heated for twenty minutes. The reaction mixture is worked up and thus 1,3-dimethyl-2,4-dioxo-7-hydroxy-6,7,8,9-tetrahydro-thiazino[2,1-f]purine is obtained; m.p.: 230°–231° C.

EXAMPLE 8

0.7 g. (2.3 mmole) of 8-(2-hydroxy-3-chloropropyl)-mercaptoltheophylline, 0.32 ml. of triethylamine and 3 ml. of n-propanol are heated for 20 minutes. 1,3-Dimethyl-2,4-dioxo-7-hydroxy-6,7,8,9-tetrahydro-thiazino[2,1-f]purine is obtained after working up the mixture. M.p.: 230° C.

EXAMPLE 9

0.5 g. (1.9 mmole) of 1,3-dimethyl-2,4-dioxo-7-hydroxy-6,7,8,9-tetrahydro-pyrimido[2,1-f]purine and 5 ml. of acetic acid anhydride are heated for 2.5 hours. After working up the mixture 1,3-dimethyl-2,4-dioxo-7-acetoxy-9-acetyl-6,7,8,9-tetrahydro-pyrimido[2,1-f]purine is obained. M.p.: 229°–230° C.

EXAMPLE 10

0.4 g. (1.4 mmole) of 1,3-dimethyl-2,4-dioxo-7-hydroxy-9-benzyl-6,7,8,9-tetrahydro-pyrimido[2,1-f]purine and 5 ml. of acetic acid anhydride are heated for 2.5 hours. After working up the mixture 1,3-dimethyl-2,4-dioxo-9-benzyl-7-acetoxy-6,7,8,9-tetrahydro-pyrimido[2,1-f]purine is obtained. M.p.: 245°–247° C.

EXAMPLE 11

0.5 g. (1.86 mmole) of 1,3-dimethyl-2,4-dioxo-7-hydroxy-6,7,8,9-tetrahydro-thiazino[2,1-f]purine and 5 ml. of acetic acid anhydride are heated for 2.5 hours. After working up the reaction mixture 1,3-dimethyl-2,4-dioxo-7-acetxy-6,7,8,9-tetrahydro-thiazino[2,1-f]purine is obtained. M.p.: 228°–229° C.

What we claim is:

1. A compound of the formula wherein
R is hydroxy, or acetyloxy Q is sulfur or a —N—R$^1$ group, wherein R$^1$ is hydrogen, C$_{1-5}$ alkyl benzyl or C$_{2-4}$ acyl,
or a pharmaceutically acceptable acid addition salt thereof.

2. 1,3-Dimethyl-2,4-dioxo-7-hydroxy-9-benzyl-6,7,8,9-tetrahydro-pyrimido[2,1-f]purine as defined in claim 1.

3. 1,3-Dimethyl-2,4-dioxo-7-hydroxy-6,7,8,9-tetrahydro-pyrimido[2,1-f]purine as defined in claim 1.

4. 1,3-Dimethyl-2,4-dioxo-7-acetoxy-9-acetyl-6,7,8,9-tetrahydro-pyrimido[2,1-f]purine as defined in claim 1.

5. 1,3-Dimethyl-2,4-dioxo-7-acetoxy-9-benzyl-6,7,8,9-tetrahydro-pyrimido[2,1-f]purine as defined in claim 1.

6. 1,3-Dimethyl-2,4-dioxo-7-acetoxy-6,7,8,9-tetrahydro-thiazino[2,1-f]purine as defined in claim 1.

7. 1,3-Dimethyl-2,4-dioxo-7-hydroxy-6,7,8,9-tetrahydro-thiazino[2,1-f]purine as defined in claim 1.

8. A compound selected from the group consisting of 1,3-dimethyl-2,4-dioxo-7-hydroxy-9-benzyl-6,7,8,9-tetrahydro-pyrimido[2,1-f]purine;

1,3-dimethyl-2,4-dioxo-7-hydroxy-6,7,8,9-tetrahydro-pyrimido[2,1-f]purine;

1,3-dimethyl-2,4-dioxo-7-acetoxy-9-acetyl-6,7,8,9-tetrahydro-pyrimido[2,1-f]purine;

1,3-dimethyl-2,4-dioxo-7-acetoxy-9-benzyl-6,7,8,9-tetrahydro-pyrimido[2,1-f]purine;

1,3-dimethyl-2,4-dioxo-7-acetoxy-6,7,8,9-tetrahydro-thiazino-[2,1-f]purine; and 1,3-dimethyl-2,4-dioxo-7-hydroxy-6,7,8,9-tetrahydro-thiazino-[2,1-f]purine.

9. A pharmaceutical composition for improving the peripheral circulation, comprising as active ingredient at least one compound of the formula I as defined in claim 1 or a pharmaceutically acceptable acid addition salt thereof admixed with the usual pharmaceutically acceptable carriers and/or solvents.

10. A method of improving peripheral circulation in an animal subject which comprises administering an effective amount of a compound defined in claim 1 or a pharmaceutically effective acid addition salts thereof in a dosage and for a period sufficient to improve circulation.